US 6,723,343 B2

(12) United States Patent
Kugelmann

(10) Patent No.: US 6,723,343 B2
(45) Date of Patent: Apr. 20, 2004

(54) PHARMACEUTICAL TRAMADOL SALTS

(75) Inventor: Heinrich Kugelmann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 12 days.

(21) Appl. No.: 10/084,682

(22) Filed: Feb. 28, 2002

(65) Prior Publication Data

US 2003/0158242 A1 Aug. 21, 2003

Related U.S. Application Data

(63) Continuation of application No. PCT/EP00/07526, filed on Aug. 3, 2000.

(30) Foreign Application Priority Data

Aug. 31, 1999 (DE) .......................................... 199 40 740

(51) Int. Cl.$^7$ ................................................. A61K 9/36
(52) U.S. Cl. ...................... 424/479; 424/490; 424/493; 424/465; 424/48; 514/222.2; 514/373
(58) Field of Search ................................ 424/479, 490, 424/493, 465, 48; 514/222.2, 373

(56) References Cited

U.S. PATENT DOCUMENTS

| | | | | |
|---|---|---|---|---|
| 3,652,589 A | | 3/1972 | Flick et al. | |
| 5,468,744 A | * | 11/1995 | Raffa et al. | 514/282 |
| 5,776,492 A | * | 7/1998 | Betzing et al. | 424/465 |
| 5,837,277 A | * | 11/1998 | Hayward | 424/441 |
| 5,919,826 A | * | 7/1999 | Caruso | 514/629 |
| 6,090,586 A | * | 7/2000 | Bergstrom et al. | 435/69.3 |
| 6,090,856 A | * | 7/2000 | Sasaki | 514/646 |
| 6,165,512 A | * | 12/2000 | Mezaache et al. | 424/489 |
| 6,562,865 B1 | * | 5/2003 | Codd et al. | 514/456 |
| 2002/0119193 A1 | * | 8/2002 | Le et al. | 424/465 |
| 2003/0035835 A1 | * | 2/2003 | Bartholomaeus et al. | 424/468 |
| 2003/0044464 A1 | * | 3/2003 | Ziegler et al. | 424/468 |

FOREIGN PATENT DOCUMENTS

| | | |
|---|---|---|
| EP | 0144960 | 6/1985 |
| WO | 98/46216 | 10/1998 |
| WO | 00/12067 | 3/2000 |

OTHER PUBLICATIONS

Buschann et al, Derwent abstract 2001–597702, 2/200.*

* cited by examiner

*Primary Examiner*—James H Reamer
(74) *Attorney, Agent, or Firm*—Crowell & Moring LLP

(57) ABSTRACT

Disclosed are a compound of tramadol and a sugar substitute, pharmaceutical compositions and sustained-release formulations comprising the compound, and methods of treatment using the compound. The tramadol compound according to the present invention has reduced bitter taste of tramadol and is more acceptable to the patient.

29 Claims, No Drawings

PHARMACEUTICAL TRAMADOL SALTS

CROSS REFERENCE TO RELATED APPLICATIONS

The present application is a continuation of international patent application no. PCT/EP00/07526, filed Aug. 3, 2000, designating the United States of America, the entire disclosure of which is incorporated herein by reference. Priority is claimed based on Federal Republic of Germany patent application no. 199 40 740.1, filed Aug. 31, 1999.

BACKGROUND OF THE INVENTION

The present invention relates to pharmaceutical salts of the active substance tramadol and at least one sugar substitute, to medicaments, or pharmaceutical compositions, containing these salts, to the use of these salts for the preparation of medicaments, and to forms of administration or pharmaceutical formulations, containing these salts.

Tramadol hydrochloride—(1RS,2RS)-2-[(dimethylamino)methyl]-1-(3-methoxyphenyl)cyclohexanol hydrochloride—is suitable for the control of intense and moderately intense pain and for the treatment of urinary incontinence. U.S. Pat. No. 3,652,589 and WO98/46216 describe the use of other salts of the active substance tramadol with inorganic acids, e.g. sulfuric acid, nitric acid or phosphoric acid, and with organic acids, e.g. benzoic acid, salicylic acid or phthalic acid, for the preparation of a medicament for the control of pain or for the treatment of urinary incontinence.

Despite the excellent efficacy of said salts in pain control, the active substance tramadol and its readily soluble salts have an intensely bitter taste. Available formulations of tramadol that releases this active substance as soon as they are taken all have this strong bitter taste. As a consequence, these immediate-release formulations are poorly accepted and patients fail to observe the dosage instructions. Although coating and complexing processes, e.g. the application of film coatings, serve to improve taste, they impede the immediate release of the active substance.

Because of the very good water solubility of tramadol hydrochloride, the preparation of sustained-release pharmaceutical forms is also made difficult. Consequently, it is necessary to use complex retardation processes, e.g. the application of sustained-release coatings or the embedding of the active substance in a sustained-release matrix.

SUMMARY AND DETAILED DESCRIPTION OF THE INVENTION

The object of the present invention was therefore to provide pharmaceutical compounds for the active substance tramadol which do not have the bitter taste of tramadol and the release of which can be retarded more effectively than that of the conventional, most widely used salt, namely tramadol hydrochloride.

According to the invention, this object is achieved by the preparation of pharmaceutical salts of the active substance tramadol and at least one sugar substitute.

The solubility of these salts in water and/or aqueous fluids is preferably $\leq 100$ mg/ml, more preferably $\leq 30$ mg/ml and particularly preferably $\leq 10$ mg/ml.

Suitable sugar substitutes are any acidic sugar substitutes which, by producing a derivative carrying at least one negative charge, are capable of forming a salt with the active substance tramadol. The sugar substitute is preferably saccharin, cyclamate, acesulfame or a mixture of at least two of these sugar substitutes.

To prepare the pharmaceutical salts according to the invention, tramadol and/or at least one very readily water-soluble salt of tramadol is reacted with at least one free acid and/or at least one water-soluble salt of at least one sugar substitute. Said salt of tramadol is preferably reacted with the water-soluble salt of the sugar substitute in an aqueous medium at neutral pH. Tramadol hydrochloride is preferably used as the salt of tramadol. The salt of the sugar substitute used is preferably the sodium, potassium, calcium or ammonium salt of saccharin and/or cyclamate and/or acesulfame. The free acid of the sugar substitute used is preferably the free acid of saccharin and/or cyclamate and/or acesulfame. If tramadol itself is reacted with the free acid of a sugar substitute, they are reacted in an organic solvent, preferably in an alkanol and more preferably in ethanol.

The invention also provides medicaments or pharmaceutical compositions which contain at least one tramadol salt according to the invention as the pharmaceutical active substance, and optionally other active substances and/or auxiliary substances.

The medicaments are preferably used for the control/treatment of pain, urinary incontinence, coughs, inflammatory and allergic reactions, depression, drug and/or alcohol abuse, gastritis, diarrhoea, cardiovascular disease, respiratory disease, mental illness and/or epilepsy.

The invention also provides the use of at least one tramadol salt according to the invention for the preparation of a medicament for the control/treatment of pain, urinary incontinence, coughs, inflammatory and allergic reactions, depression, drug and/or alcohol abuse, gastritis, diarrhoea, cardiovascular disease, respiratory disease, mental illness and/or epilepsy.

The amount of active substance to be administered to the patient varies according to the patient's weight, the type of administration, the indication and the degree of severity of the disease. Conventionally, at least one tramadol salt according to the invention is administered in amounts in which the content of the active substance tramadol corresponds to 1 to 600 mg/day.

The invention also provides for pharmaceutical formulations containing at least one tramadol salt according to the invention.

The amounts of tramadol and sugar substitute in the pharmaceutical compositions or formulations according to the invention are to be chosen so that the bitter taste of the active substance tramadol is compensated by the taste of the sugar substitute. The forms of administration according to the invention preferably contain the sugar substitute and the tramadol in equimolar amounts, i.e. the two components are virtually completely in salt form. The forms of administration according to the invention can also contain the tramadol and sugar substitute in different molar amounts according to the sweetness of the sugar substitute used and/or the desired release profile for the tramadol.

The forms of administration according to the invention can be solid, semisolid or liquid, preferably oral medicament formulations which, in addition to the salt of the active substance tramadol and at least one sugar substitute, optionally contain other active substances and the conventional auxiliary substances, excipients and additives.

The solid forms of administration according to the invention are preferably multiparticulate formulations, particularly preferably in the form of granules, microparticles, microtablets or pellets and optionally filled into capsules or in the form of tablets, preferably rapidly disintegrating tablets or effervescent tablets, the tablets preferably having been compressed from pellets or produced by hot-melt extrusion.

If the solid forms of administration according to the invention are intended for release of the active substances via the intestinal tract, they preferably need to have at least one enteric coating which dissolves as a function of pH. Because of this coating, said forms pass through the stomach undissolved and the active substance(s) is (are) only released in the intestinal tract.

The forms of administration according to the invention are also preferably formulated as a gel, a chewing gum, a juice, particularly preferably an oil-based or water-based juice, or a spray, particularly preferably a sublingual spray.

A preferred embodiment of the forms of administration according to the invention, for release of the tramadol via the stomach, comprises oil-based or water-based juices, which release the active substance(s) without delay.

A retardation and hence also a further modification of the release of the active substance tramadol, and optionally other active substances, can be effected by the application of at least one sustained-release coating, the embedding of the salt of the active substance in at least one sustained-release matrix, or a combination thereof.

Retardation of release is preferably achieved with the aid of sustained-release coatings. Suitable sustained-release coatings include water-insoluble waxes or polymers, e.g. acrylic resins, preferably poly(meth)acrylates, or water-insoluble celluloses, preferably ethyl cellulose. These materials are well-known to those of ordinary skill in the art. See, e.g. Bauer, Lehmann, Osterwald, Rothgang "Überzogene Arzneiformen" ("Coated pharmaceutical forms"), Wissenschaftliche Verlagsgesellschaft mbH Stuttgart, 1988, pp. 69 et seq., which is incorporated herein by reference.

To adjust the rate of release of the active substance, the sustained-release coatings can optionally contain, in addition to the water-insoluble polymers, non-retarding, preferably water-soluble polymers in amounts of up to 30 wt. %, such as polyvinylpyrrolidone or water-soluble celluloses, preferably hydroxypropyl methyl cellulose or hydroxypropyl cellulose, and/or hydrophilic pore-forming agents such as sucrose, sodium chloride or mannitol, and/or the known plasticizers.

To retard the salt of the active substance, the forms of administration according to the invention can also preferably contain said salt in a sustained-release matrix, preferably as a uniform distribution.

Matrix materials which can be used are physiologically compatible, hydrophilic materials known to those skilled in the art. Hydrophilic matrix materials used are preferably polymers and particularly preferably cellulose ethers, cellulose esters and/or acrylic resins. Matrix materials used are very particularly preferably ethyl cellulose, hydroxypropyl methyl cellulose, hydroxypropyl cellulose, hydroxymethyl cellulose, poly(meth)acrylic acid and/or derivatives thereof such as their salts, amides or esters.

Other preferred matrix materials are those comprising hydrophobic materials such as hydrophobic polymers, waxes, fats, long-chain fatty acids, fatty alcohols or corresponding esters or ethers, or mixtures thereof. The hydrophobic materials used are particularly preferably $C_{12}$–$C_{30}$ fatty acid mono- or diglycerides and/or $C_{12}$–$C_{30}$ fatty alcohols and/or waxes, or mixtures thereof.

The sustained-release matrix material used can also be mixtures of said hydrophilic and hydrophobic materials.

The forms of administration according to the invention can be produced by various methods known to those skilled in the art, See, e.g. "Pharmaceutical Pelletization Technology", Drugs and the Pharmaceutical Sciences vol. 37, Verlag Marcel Decker, or "Remington's Pharmaceutical Sciences", Mack Publishing Company, Easton, Pa., which are herein incorporated by reference.

If the forms of administration according to the invention, e.g. tablets or pellets, have coatings, these can be applied by conventional processes, e.g. by the coating pan process, by the spraying of solutions, dispersions or suspensions, by the hot-melt process or by the powder application process.

From forms of administration according to the invention which are used to release the tramadol via the oral mucosa, e.g. from a gel, a chewing gum or a sublingual spray, a substantially constant release of the tramadol is achieved without the use of a sustained-release matrix and/or a sustained-release coating.

From forms of administration according to the invention which are used to release the tramadol via the intestinal tract, e.g. from capsules, tablets, granules or pellets, a constant release of the tramadol is again achieved without the use of a sustained-release matrix and/or a sustained-release coating, but with the provision of an enteric coating.

The forms of administration according to the invention also have the advantage that the intensely bitter taste of tramadol is mitigated by the simultaneous release of a sugar substitute. This increases the patients' acceptance of the medicaments containing the active substance tramadol and improves observance of the dosage instructions.

The medicaments according to the invention are also suitable for diabetics.

The formation of a salt from tramadol and a sugar substitute and/or an auxiliary substance with a solubility of $\leq 100$ mg/ml in water and/or aqueous body fluids affords a more effective retardation of the release of the active substance tramadol using conventional retardation processes, compared with tramadol hydrochloride.

Sustained-release medicaments which contain these tramadol salts according to the invention can therefore be produced more simply and more cost-effectively. This also applies to other modifications of the medicaments according to the invention, e.g. those with enteric coatings.

The solubility of the salts of tramadol and a sugar substitute was determined as follows:

The salt of (1RS,2RS)-2-[(dimethylamino)methyl]-1-(3-methoxyphenyl)cyclohexanol and the appropriate sugar substitute was placed at 25° C. in deionized water in an amount (e.g. approx. 1 g of tramadol saccharinate to 10 ml of deionized water) to form a saturated solution at this temperature which was still saturated after being stirred for 20 hours at 25° C. The requisite amount of the salt of tramadol and the appropriate sugar substitute can optionally be determined by preliminary experiments.

After the undissolved salt of tramadol and the appropriate sugar substitute had been allowed to settle out, the clear supernatant was pipetted off and centrifuged for 5 minutes at a speed of at least 3000 rpm. Part of the resulting clear supernatant is transferred to an HPLC sample vial and the concentration of the salt of tramadol and the appropriate sugar substitute is determined against tramadol hydrochloride as standard.

The invention is illustrated below with the aid of the Examples. The illustrations are given solely by way of example and do not limit the general spirit of the invention.

EXAMPLE 1

To prepare tramadol saccharinate, 30.0 g (0.1 mol) of tramadol hydrochloride and 20.53 g (0.1 mol) of saccharin sodium or 24.13 g (0.1 mol) of saccharin sodium dihydrate were completely dissolved in the minimum amount of water, with heating in both cases. The two solutions were then mixed together, with stirring. On cooling, the tramadol saccharinate crystallized out of the aqueous solution after only a short time and was isolated by conventional methods and purified with ethanol.

The solubility of the resulting tramadol saccharinate in water was determined by the method indicated above and is 22.5 mg/ml.

EXAMPLE 2

30.0 g (0.1 mol) of tramadol hydrochloride were dissolved in 20 g of water and mixed slowly with a solution of 20.13 g (0.1 mol) of sodium cyclamate in 36 g of water, with stirring. The resulting solution was then stored for 16 hours at a temperature of 5° C. The tramadol cyclamate was obtained in crystalline form, isolated by conventional methods and purified with ethanol.

EXAMPLE 3

30.0 g (0.1 mol) of tramadol hydrochloride were dissolved in 13 g of water and mixed slowly with a solution of 20.13 g (0.1 mol) of acesulfame potassium in 53 g of water, with stirring. The resulting solution was then stored overnight at 5° C. The tramadol acesulfamate was obtained in crystalline form, isolated by conventional methods and purified with ethanol.

EXAMPLE 4

An oral gel was prepared by first dissolving 0.33 g of methylparaben, 0.05 g of propylparaben and 75.0 g of xylitol in 197.63 g of purified water at a temperature of 80° C. and then cooling the mixture to 40° C. 0.75 g of tramadol saccharinate was then added, with stirring, followed by 2 g of xanthan gum, the mixture was stirred for a further one hour and water lost by evaporation was replaced. After cooling to room temperature, the mixture was flavoured with 0.625 g of Orange-Mandarin Flavor 10888-56 (Givaudan Roure Flavors Ltd., CH 8600 Duibendorf, Germany), with stirring.

EXAMPLE 5

5 g of comminuted chewing gum mass (Popeye Amural Confections, Yorkville, Ill.) were heated to a temperature of 30 to 40° C. in a Fanta dish. Using a pestle, 150 mg of tramadol saccharinate were then incorporated into the viscous chewing gum mass. The homogeneous mass was then divided up into 1 g portions in teflon-coated moulds.

For a comparative taste test, chewing gums were prepared by the same process with the stoichiometrically equivalent amount of tramadol (corresponding to 100 mg of tramadol hydrochloride).

The result of the taste test was that the chewing gums containing the tramadol hydrochloride had an intolerably bitter taste after only a short time and could not be chewed any longer. The chewing gums containing the tramadol saccharinate had an excellent taste at the beginning and were still enjoyable even after prolonged chewing.

EXAMPLE 6

To prepare a water-based juice, 0.33 g of methylparaben, 0.05 g of propylparaben and 75.0 g of xylitol were dissolved in 198.37 g of purified water at a temperature of 80° C. The mixture was cooled to 40° C. and 0.75 g of tramadol saccharinate was added, with stirring. 0.25 g of xanthan gum was then added, the mixture was stirred for an addition hour and water lost by evaporation was replaced. After cooling to room temperature, the mixture was flavored with 0.075 g of Tutti Frutti 9/008897 (Dragoco Gerberding & Co. AG, 37603 Holzminden, Germany), with stirring.

EXAMPLE 7

To prepare an oil-based juice, 0.33 g of methylparaben and 0.05 g of propylparaben were dissolved at a temperature of 80° C. in 209.88 g of glycerol esterified with saturated $C_{8-10}$ fatty acids. The mixture was cooled to 25° C. and 37.5 g of ground xylitol, 1.25 g of highly disperse silicon dioxide and 0.75 g of tramadol saccharinate were suspended therein, with stirring. The mixture was then flavored with 0.0125 g of Blood Orange 9/028658 (Dragoco Gerberding & Co. AG, 37603 Holzminden, Germany), with stirring.

EXAMPLE 8

A sublingual spray was prepared by first dissolving 0.33 g of methylparaben, 0.05 g of propylparaben and 75.0 g of xylitol in 197.37 g of distilled water at a temperature of 80° C. The solution was cooled to 40° C. and 0.75 g of tramadol saccharinate was added. 0.15 g of xanthan gum was then added, the mixture was stirred for an additional hour and water lost by evaporation was replaced. The solution was cooled to 25° C. and flavored with 0.75 g of Grapefruit 14391786 (IFF, International Flavors & Fragrances GmbH, 46446 Emmerich, Germany).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. A pharmaceutically acceptable salt of tramadol and a sugar substitute, wherein the solubility of the salt in water or aqueous body fluids is <100 mg/ml.

2. A salt according to claim 1, wherein the solubility is ≦30 mg/ml.

3. A salt according to claim 2, wherein the solubility is ≦10 mg/ml.

4. A salt according to claim 1, wherein the sugar substitute is saccharin, cyclamate or acesulfame.

5. A pharmaceutical composition comprising a salt according to claim 1, and a pharmaceutically acceptable excipient.

6. A method for the treatment of one or more of pain, urinary incontinence, coughs, inflammatory and allergic reactions, depression, drug and alcohol abuse, gastritis, diarrhea, cardiovascular disease, respiratory disease, mental illness and epilepsy, comprising administering an effective amount of the pharmaceutical composition according to claim 5 to a patient in need thereof.

7. A method according to claim 6, wherein the method is for the control of pain.

8. A method according to claim 6, wherein the method is for the treatment of urinary incontinence.

9. A method according to claim 6, wherein the method is for the treatment of coughs.

10. A method according to claim 6, wherein the method is for the treatment of inflammatory and allergic reactions.

11. A method according to claim 6, wherein the method is for the treatment of depression.

12. A method according to claim 6, wherein the method is for the treatment of drug and/or alcohol abuse.

13. A method according to claim 6, wherein the method is for the treatment of gastritis.

14. A method according to claim 6, wherein the method is for the treatment of diarrhea.

15. A method according to claim 6, wherein the method is for the treatment of cardiovascular disease.

16. A method according to claim 6, wherein the method is for the treatment of respiratory disease.

17. A method according to claim 6, wherein the method is for the treatment of mental illness.

18. A method according to claim 6, wherein the method is for the treatment of epilepsy.

19. A pharmaceutical composition according to claim 5, further comprising an additional active substance.

20. A pharmaceutical composition according to claim 5, wherein the pharmaceutical composition is a multiparticulate formulation.

21. A pharmaceutical composition according to claim 20, wherein the multiparticulate formulation is selected from the group consisting of granules, microparticles, microtablets and pellets.

22. A pharmaceutical composition of claim 21, wherein the pharmaceutical composition is filled into capsules or in the form of tablets, rapidly disintegrating tablets or effervescent tablets, or in the form of pellets compressed to tablets.

23. A pharmaceutical composition of claim 22, wherein the pharmaceutical composition comprises at least one enteric coating.

24. A pharmaceutical composition of claim 21, wherein the pharmaceutical composition is formulated as a gel, a chewing gum, a juice or a spray.

25. A pharmaceutical composition of claim 24, wherein the spray is a sublingual spray.

26. A pharmaceutical composition of claim 21, wherein the pharmaceutical composition comprises at least one sustained-release matrix.

27. A pharmaceutical composition of claim 21, wherein the pharmaceutical composition comprises at least one sustained-release coating.

28. A pharmaceutical composition of claim 24, wherein the juice is an oil-based juice.

29. A pharmaceutical composition of claim 24, wherein the juice is a water-based juice.

* * * * *